United States Patent
Duckett et al.

(10) Patent No.: US 12,201,272 B2
(45) Date of Patent: Jan. 21, 2025

(54) IMAGING APPARATUS AND VIDEO ENDOSCOPE PROVIDING IMPROVED DEPTH OF FIELD AND RESOLUTION

(71) Applicants: KARL STORZ SE & Co. KG, Tuttlingen (DE); KARL STORZ Imaging, Inc., Goleta, CA (US)

(72) Inventors: George Duckett, Castaic, CA (US); Eric Hale, Vancouver, WA (US); Nathan Schara, Washougal, WA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 684 days.

(21) Appl. No.: 17/498,108

(22) Filed: Oct. 11, 2021

(65) Prior Publication Data
US 2022/0026725 A1    Jan. 27, 2022

Related U.S. Application Data (63) Continuation of application No. 16/362,886, filed on Mar. 25, 2019, now Pat. No. 11,163,169.

(51) Int. Cl.
*G02B 27/10*    (2006.01)
*A61B 1/00*    (2006.01)
(Continued)

(52) U.S. Cl.
CPC ........ *A61B 1/051* (2013.01); *A61B 1/000095* (2022.02); *A61B 1/00096* (2013.01);
(Continued)

(58) Field of Classification Search
None
See application file for complete search history.

(56) References Cited

U.S. PATENT DOCUMENTS

| | | | |
|---|---|---|---|
| 4,801,792 A | 1/1989 | Yamasita | |
| 5,150,234 A * | 9/1992 | Takahashi | G02F 1/29 349/1 |

(Continued)

FOREIGN PATENT DOCUMENTS

| | | |
|---|---|---|
| EP | 0602923 A1 | 6/1994 |
| EP | 2868254 A1 | 5/2015 |

(Continued)

OTHER PUBLICATIONS

Mertens, et al., "Exposure Fusion," Computer Graphics and Applications, 2007, pp. 1-9.

(Continued)

*Primary Examiner* — John P Leubecker
(74) *Attorney, Agent, or Firm* — David N. Villalpando; Jacqueline Cohen (57) ABSTRACT

A dynamic imaging system for use with endoscope, or as an element of a video endoscope, utilizes path length differences and/or a variable aperture size to expand a usable depth of field and/or improve image resolution in an area of interest in the image field. In some implementations, the imaging system utilizes a variable aperture in conjunction with unequally spaced image sensors placed downstream from a beam splitter. An imaging system captures multiple focal planes of an image scene on separate sensors. A variable aperture permits the capture of enhanced resolution images or images with longer depths of field. These differently focused images and/or images with different resolutions and depths of field are then combined using image fusion techniques.

14 Claims, 11 Drawing Sheets

(51) Int. Cl.

| | | |
|---|---|---|
| *A61B 1/04* | (2006.01) | |
| *A61B 1/05* | (2006.01) | |
| *G02B 23/24* | (2006.01) | |
| *G02B 27/28* | (2006.01) | |
| *H04N 23/45* | (2023.01) | |
| *H04N 23/55* | (2023.01) | |
| *H04N 23/951* | (2023.01) | |
| *H04N 23/50* | (2023.01) | |

(52) U.S. Cl.
CPC ...... *A61B 1/00186* (2013.01); *A61B 1/00188* (2013.01); *A61B 1/0019* (2013.01); *A61B 1/042* (2013.01); *G02B 23/2446* (2013.01); *G02B 27/1066* (2013.01); *G02B 27/283* (2013.01); *H04N 23/45* (2023.01); *H04N 23/55* (2023.01); *H04N 23/951* (2023.01); *H04N 23/555* (2023.01)

(56) References Cited

U.S. PATENT DOCUMENTS

| | | | |
|---|---|---|---|
| 5,608,451 A | 3/1997 | Konno | |
| 5,793,539 A | 8/1998 | Konno | |
| 5,876,327 A * | 3/1999 | Tsuyuki | A61B 1/00096 |
| | | | 600/181 |
| 5,944,655 A | 8/1999 | Becker | |
| 6,069,651 A * | 5/2000 | Tsuyuki | G02B 23/2423 |
| | | | 348/75 |
| 6,880,943 B2 | 4/2005 | Fiete | |
| 6,924,935 B2 | 8/2005 | Miller | |
| 6,943,946 B2 | 9/2005 | Fiete | |
| 8,784,301 B2 | 7/2014 | McDowall | |
| 8,878,919 B2 | 11/2014 | Tsuyuki | |
| 8,988,516 B2 | 3/2015 | Sasamoto | |
| 8,994,802 B2 | 5/2015 | Suga | |
| 9,030,543 B2 | 5/2015 | Tsuyuki | |
| 2001/0022687 A1 | 9/2001 | Takahashi | |
| 2007/0156021 A1 | 7/2007 | Morse | |
| 2008/0079897 A1 | 4/2008 | Goldfain | |
| 2009/0076329 A1 | 3/2009 | Su | |
| 2010/0157019 A1 | 6/2010 | Schwotzer | |
| 2010/0194870 A1 * | 8/2010 | Ghita | G01B 11/22 |
| | | | 348/E5.045 |
| 2012/0033094 A1 * | 2/2012 | Ishii | G06T 5/73 |
| | | | 348/208.6 |
| 2012/0105612 A1 * | 5/2012 | Yoshino | A61B 1/00163 |
| | | | 348/E5.045 |
| 2013/0041215 A1 * | 2/2013 | McDowall | G02B 27/283 |
| | | | 600/109 |
| 2013/0041216 A1 * | 2/2013 | McDowall | G02B 6/001 |
| | | | 600/109 |
| 2013/0041226 A1 * | 2/2013 | McDowall | H04N 13/239 |
| | | | 600/166 |
| 2013/0083386 A1 * | 4/2013 | Harding | A61B 1/045 |
| | | | 359/240 |
| 2013/0271587 A1 * | 10/2013 | Tsuyuki | A61B 1/051 |
| | | | 348/71 |
| 2013/0271763 A1 * | 10/2013 | Li | G02B 27/0075 |
| | | | 356/369 |
| 2014/0085421 A1 | 3/2014 | Kuth | |
| 2014/0176692 A1 * | 6/2014 | Tsuyuki | H04N 23/56 |
| | | | 348/71 |
| 2014/0198194 A1 | 7/2014 | Suga | |
| 2014/0333802 A1 * | 11/2014 | Arai | H04N 23/951 |
| | | | 348/239 |
| 2015/0309284 A1 * | 10/2015 | Kagawa | A61B 1/00 |
| | | | 348/76 |
| 2017/0049306 A1 * | 2/2017 | Katakura | A61B 1/00096 |
| 2017/0086657 A1 * | 3/2017 | Bodor | A61B 1/00188 |

FOREIGN PATENT DOCUMENTS

| | | | |
|---|---|---|---|
| EP | 2891448 A1 | 8/2015 | |
| EP | 2375967 B1 | 8/2016 | |
| JP | 06342122 A * | 12/1994 | |
| JP | 2003078802 A * | 3/2003 | |
| JP | 2006242976 A | 9/2006 | |
| JP | 4226235 B2 | 3/2014 | |
| WO | 2013025530 A1 | 2/2013 | |

OTHER PUBLICATIONS

Burt, P. J., and E. H. Adelson, "A Multiresolution Spline with Application to Image Mosaics," ACM Trans. on Graphics, 1983, vol. 2, No. 4, pp. 217-236.

Sufi, A., "Combining Exposure and Focus Fusion," Technical Paper Presentation, 2010, pp. 1-31, Rutgers University, New Brunswick.

McAlpine, K., "A better 3D Camera with Clear, Graphene Light Detectors," University of Michigan News, 2016, pp. 1-3, Ann Arbor.

* cited by examiner

IMAGING APPARATUS AND VIDEO ENDOSCOPE PROVIDING IMPROVED DEPTH OF FIELD AND RESOLUTION

CROSS-REFERENCE TO RELATED APPLICATION

This application is a continuation of U.S. application Ser. No. 16/362,886, filed Mar. 25, 2019, entitled, "Endoscope and Imaging Arrangement Providing Improved Depth of Field and Resolution," that issued as U.S. Pat. No. 11,163,169 B2 on Nov. 2, 2021, which is a continuation-in-part of U.S. application Ser. No. 15/175,520, filed on Jun. 7, 2016, and issued on Jun. 18, 2019, as U.S. Pat. No. 10,324,300 B2 entitled "Endoscope and Imaging Arrangement Providing Depth of Field," all of the forgoing are hereby incorporated by reference.

BACKGROUND OF THE INVENTION

Field of the Invention

The presently disclosed device is directed to an endoscope capable of producing views with increased depth of field. The endoscope can utilize a variety of beam splitters combined with polarization filters and beam-shapers to provide separate imaging channels to separate sensors.

Description of the Background Art

Conventionally, endoscopes were monocular providing images through long telescoping lens arrangements. Initially, they allowed doctors to view inside patients with their eyes. These simple devices relayed images but did not provide depth information. As video-assisted surgery progressed, depth and size information was increasingly necessary, particularly, for tumor and thrombosis identification and assessment.

The monocular endoscopes were modified to take in two views at the head and switch between each view, transmitting each one across a conventional single channel lens to a single sensor. For instance, the device described in U.S. Pat. No. 5,944,655 to Becker is exemplary. These devices provided stereoscopic views for doctors but required thicker heads to accommodate the separate imaging capturing lenses, beam combiners and high-speed apertures. This made smaller scale applications difficult to produce.

Alternatively, some devices provided two separate channels for each view and separate sensors in a mirrored configuration much like two side-by-side monocular endoscopes. This arrangement conserves head volume but at the expense of a thicker channel between the head and the sensor. The device disclosed in US 2014/085421 is exemplary of the state of the art. These two separate channels still only provide stereoscopic views; not three-dimensional information or depth of field information.

Figure 1:
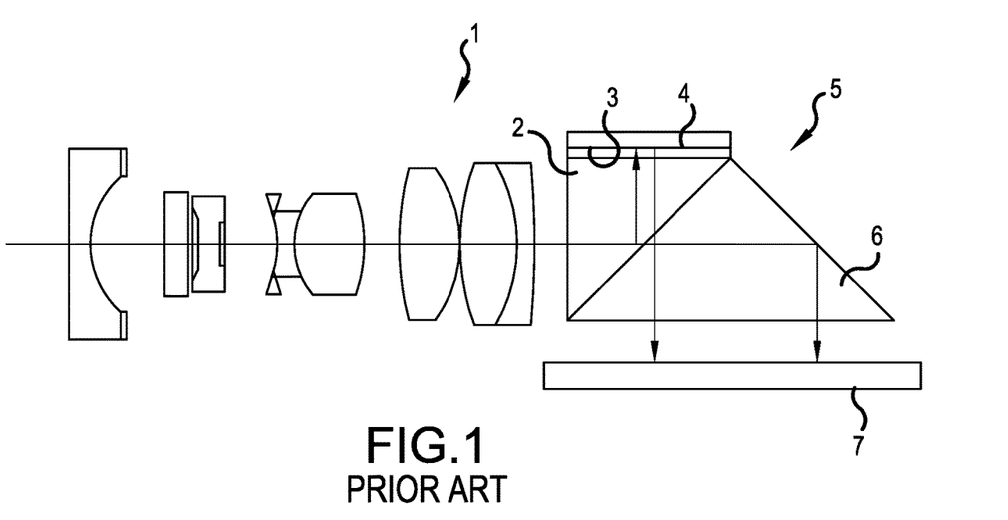
FIG. 1 shows a known endoscope lens arrangement.

Another endoscope arrangement is disclosed in US 2014/0198194. This arrangement uses only a single image formation and transmittal channel, but splits the channel at the image sensing end. FIG. 1 of US 2014/0198194 is illustrated in FIG. 1 of this disclosure. The beam splitter 5 at the distal end of the endoscope 1 divides the incoming captured light into two channels. The first channel is reflected upwards by the first interface of the prism 2 and polarized by the λ/4 waveplate 4 before being reflected by mirror 3 back to the sensor 7. The second channel passes through the interface and through the second prism 6 to a second interface and is reflected down to the sensor 7.

Endoscope 1 of US 2014/0198194 also provides two views from the two imaging channels. Each channel is separately focused due to path length differences within the prism. These separate channels allow for a depth of field to be reconstructed from the two separately focused images. However, the depth of field difference provided by the device of FIG. 1 is static. Thus, depth information can only be provided at two focal planes. This limits the amount of in-focus image information which can be utilized from the two images.

SUMMARY OF THE INVENTION

The invention disclosed herein relates to a dynamic imaging system for adjusting path length differences to expand a usable depth of field for an endoscope. The imaging system utilizes a variable lens to adjust the focal plane of the beam or an actuated sensor to adjust the detected focal plane. The imaging system is thus capable of capturing and adjusting the focal plane of separate images captured on separate sensors. The separate light beams may be differently polarized by a variable wave plate or a polarized beam splitter to allow separate manipulation of the beams.

The imaging system can be designed for easy attachment to an endoscope. The optics can be adapted to receive images at a number of sensors by splitting the incoming beam. Different beam splitter configurations are provided to deliver two or more beams of different path lengths to different sensors. These captured images with different focal planes require additional processing to generate a combined image.

The image fusion methods of Mertens, et al. "Exposure Fusion" by Mertens, et al. in Computer Graphics and Applications (2007) and Burt, et al. "A Multiresolution Spline With Application to Image Mosaics" ACM Transactions on Graphics, Vol. 2. No. 4, October 1983, p. 217-236 are adapted to combine the differently focused images of the imaging system into one clearer image. The combination of these processes can handle focal variations (far and near) as well as exposure differences (over and under). First the fusion method generates a contrast weight map, a saturation weight map and an exposure weight map for each captured image. Second, these maps are applied to select the best pixels from each image. Finally, the separate weighted images containing the selected or weighted pixels are combined with pyramid-based image fusion. The journal article "Exposure Fusion" by Mertens, et al. in Computer Graphics and Applications (2007) is incorporated herein by reference. Likewise, Burt, et al. "A Multiresolution Spline With Application to Image Mosaics" ACM Transactions on Graphics, Vol. 2. No. 4, October 1983, p. 217-236 is incorporated herein by reference.

The imaging system is placed in an adaptable camera head for an endoscope, such that the camera head can be placed on a variety of endoscopes. In addition to the beamsplitting and polarizing optics, the camera head would include Radio Frequency Identification receiver for detecting the endoscope end and aiding in the coupling procedure. Upon detection of the particular endoscope being used, the imaging system would adapt the sensor positions and other optical elements as necessary to use the light beam from the particular endoscope.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 2:
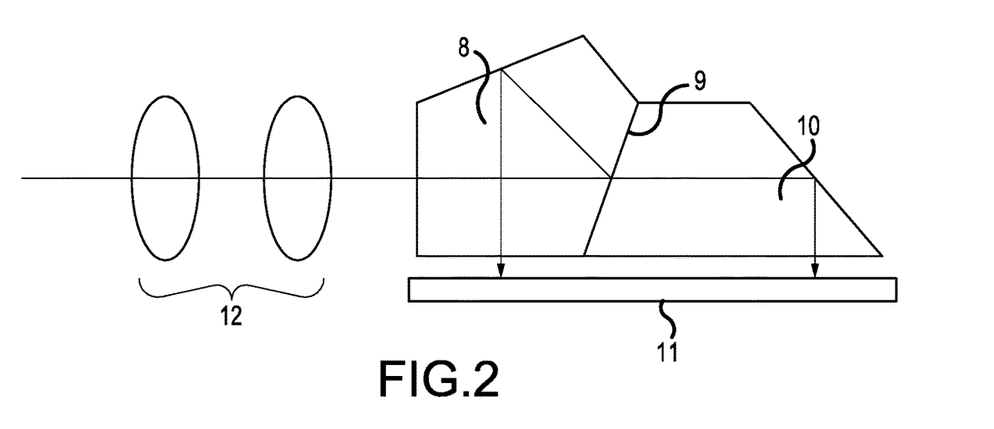
FIG. 2 shows a first beam splitter and imaging arrangement.

The beam splitter of FIG. 2 receives a beam of light from a carrier lens 12. The beam enters the pentaprism 8 and is partially reflected off a first interface 9 and then internally reflected back towards a sensor 11. The remaining light passing through the interface is reflected off a back surface of a prism 10 towards the same sensor 11. The first interface 9 can be a half-silvered mirror or semi-reflective coating on one of the prism surfaces.

Each reflection changes the path length and, as a result, the back focal length of each beam is different. The image formed on each portion of the sensor 11 captures a separate focal plane of the object being observed by the insertion portion of an endoscope. Alternatively, two separate sensors can be used in place of the single sensor 11, and the individual sensors can be placed at different distances from the beam splitter.

Figure 3:
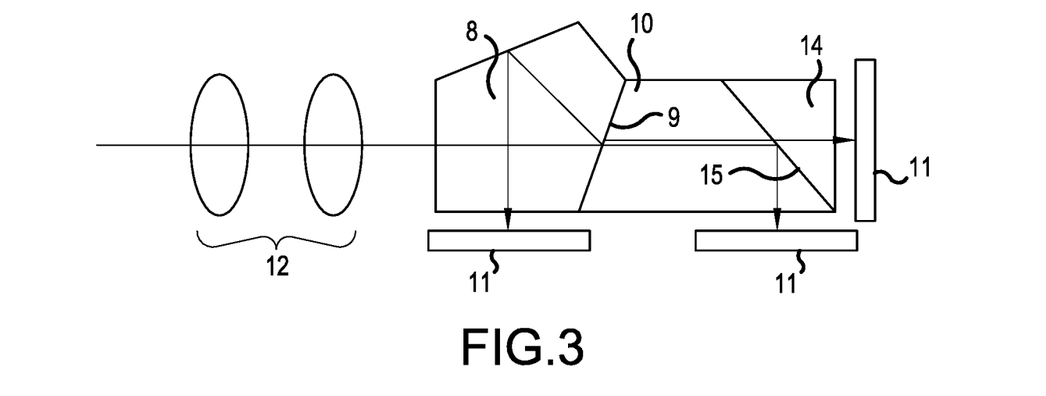
FIG. 3 shows a second beam splitter and imaging arrangement.

The beam splitter of FIG. 3 includes the beam splitter of FIG. 2 along with prisms 8 and 10 with an additional rear prism 14. This arrangement further splits the remaining light passing through the interface 15. The interface 15 can be ⅔ reflective or 50% reflective and the sensors 11, individually detecting each partial beam, can be offset from the prisms at different distances. The additional interface 15 provides a third beam which is captured by a third sensor 11 for additional depth of field information.

Each separate sensor 11 detects a differently focused beam providing an image including information at a particular depth. Each of the beam splitter elements or prisms (8, 10 and 14), can be made of crystal glass, polymers, acrylic, or other light transmissive materials. Also, the interfaces (9, 15) can be made partially reflective such that the intensity of each sensed beam is substantially equal. Alternatively, to compensate for surface losses or other differences, the reflective surfaces on the interfaces (9,15) may divide the beams unequally.

Figure 4:
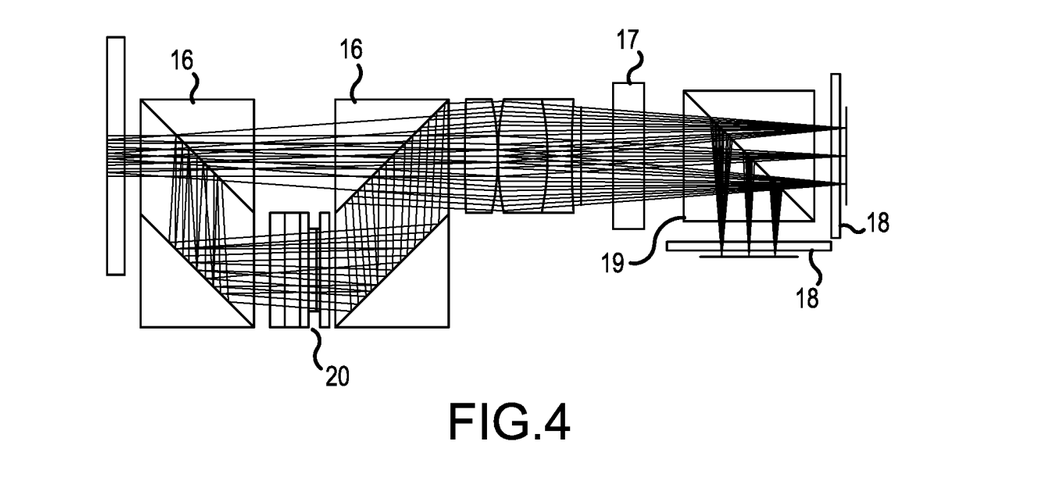
FIG. 4 shows an imaging head of an endoscope.

The optical arrangement of FIG. 4 describes an imaging head for an endoscope, including polarizing beam splitter 16 with a polarizing function, variable liquid lens 20, temporally-switched variable waveplate 17, beam splitter 19 and sensors 18. The first beam splitter 16 separates the light exiting a detachable endoscope into two channels. A focus difference is introduced between the two channels while they are separate using the variable liquid lens 20. The two channels are then recombined spatially while maintaining their distinct polarizations.

Both channels pass through a gap in which the variable liquid lens 20 is disposed. After passing through this gap, both channels enter another beam splitter 16 recombines the two beams and passes them on to a variable wave plate 17 for changing the polarization of both beams. The variable wave plate 17 varies between ON and OFF such that when it is ON, the polarization of the incoming light beam is rotated by 90 degrees.

After the variable wave plate 17, the combined beam enters a beam splitter 19 which once again separates the channels based on polarization such that they are imaged onto different sensors 18. Thus, on odd frames, one sensor 18 captures "s" polarized light and the other sensor 18 captures "p" polarized light. On even frames, the different sensors 18 are given the other channel. The collimating lens group 22 is disposed before the variable wave plate 17 for further beam manipulation and control.

In this manner, four different images corresponding to four different focal planes can be acquired over the course of two frames. From the plurality of images, a processing unit (not shown) calculates an image with greater depth of field than would be possible with a single sensor and conventional optics. Alternatively, this imaging head could be integrated into a video endoscope that does not detach from a camera head.

Figure 5:
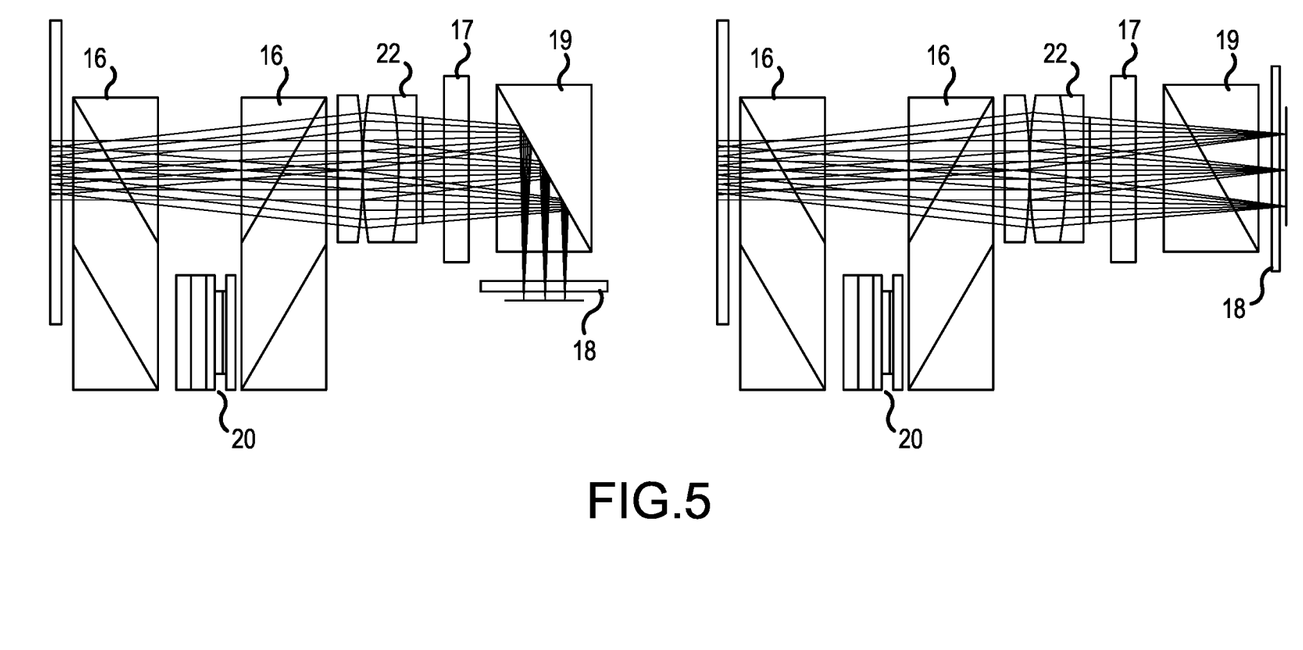
FIG. 5 shows two separate imaging channels to one of the sensors of the imaging head of FIG. 4.
Figure 6:
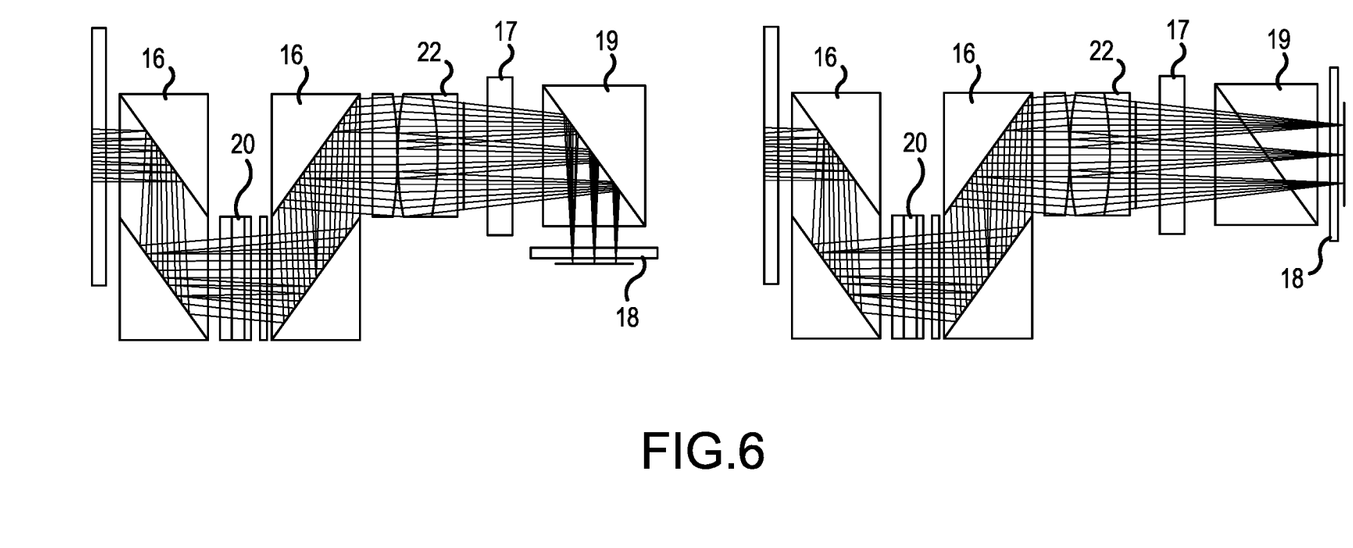
FIG. 6 shows two additional imaging channels to the other sensor of the imaging head of FIG. 4.

The two illustrations in FIG. 5 show the two beam paths taken by the first channel during separate capture frames, that is on odd/even frames. Likewise, the two illustrations in FIG. 6 show the two beam paths taken by the second channel during separate capture frames. The beams in FIG. 5 have different focal planes due to a difference in offset of the sensors 18 from the beam splitter 19. Likewise, beams in FIG. 6 have different focal planes due to a difference in offset of the sensors 18 from the beam splitter 19.

The focal difference between the first and second channels due to the variable lens 20 and path length difference is also simultaneously provided to the sensors 18. This results in four unique focal planes over two capture periods. Furthermore, the variable lens can change position or focal power to increase the number of focal planes further or simply to adjust focus. The variable lens may have variable curvature or a variable index of refraction.

The camera head may also have a control unit to adjust the focal difference according to the content of the acquired image, the imaging environment, or other application specific needs. In addition, the camera head can be capable of identifying the specific endoscope or endoscope-type being used and adjust focus accordingly. The "s" and "p" polarization described above is exemplary and could be replaced with circular or elliptical polarization.

Figure 7:
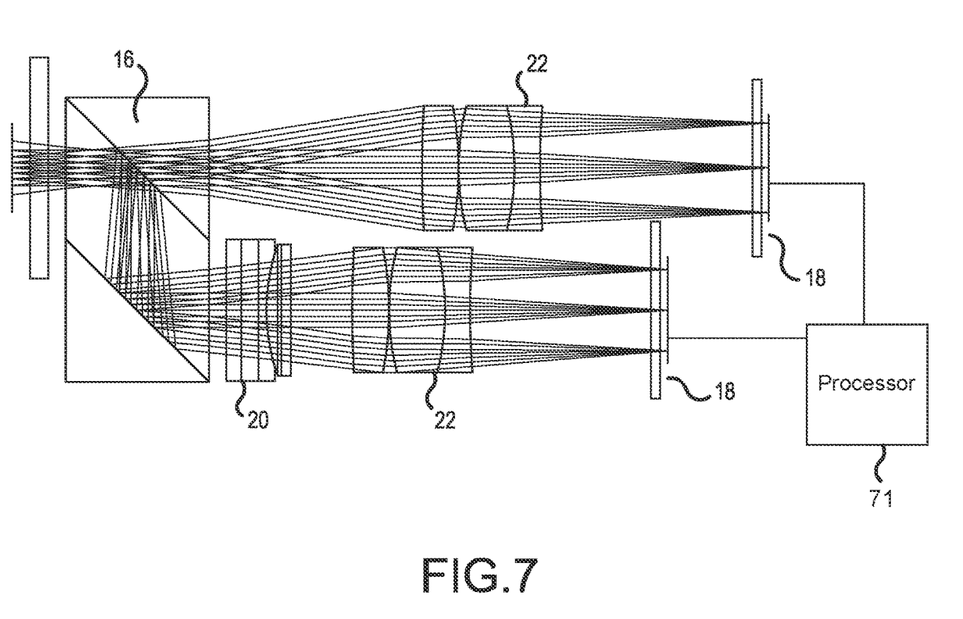
FIG. 7 shows an alternatively arranged imaging head of an endoscope.

The camera head of FIG. 7 includes a single beam splitter 16, a variable lens 20, two collimating lens groups 22, and two sensors 18. The function of the camera head is similar to that of FIGS. 4-6 with no recombination of the two channels by an additional beam splitter 16. This configuration is easier to manufacture but only acquires two images per acquisition period.

In the arrangement of FIG. 7, the light beam from the endoscope enters the beam splitter 16 and is divided into two beams. The first beam passes through a collimating lens group 22 before impinging on the image sensor 18. Separately, the second beam passes through a variable lens 20 and then another separate collimating lens group 22 before impinging on image sensor 18.

The arrangement is also connected to a control device for controlling the variable lens and a processor 71 that calculates depth from the captured images or segments the in-focus portions for recombination and display. The processor 71 is also able to model three-dimensional surfaces and build complex tissue models. These models and surfaces can be stored in memory such as RAM or transmitted to a display screen for display to a user.

Conventional methods to increase depth of field fundamentally decrease the resolution. Thus, typically systems are forced to make a tradeoff between depth of field and resolution. However, combining several image sensors to provide depth information preserves resolution and can even improve it. Furthermore, the images can be segmented to provide the in-focus portion of each captured image and recombine the in-focus segments for a clearer image with more depth information and depth of field.

Additionally, the camera head of FIG. 7 can include an aperture stop smaller than the exit pupil of the endoscope. This increases the depth of field but also reduces the resolution. Alternatively, the camera head could provide a fixed offset between focal planes. However, to provide a fixed offset across different endoscopes, the camera head would need to adjust to each endoscope type. The camera head can be integrated into or detachable from a video-endoscope.

Figure 8:
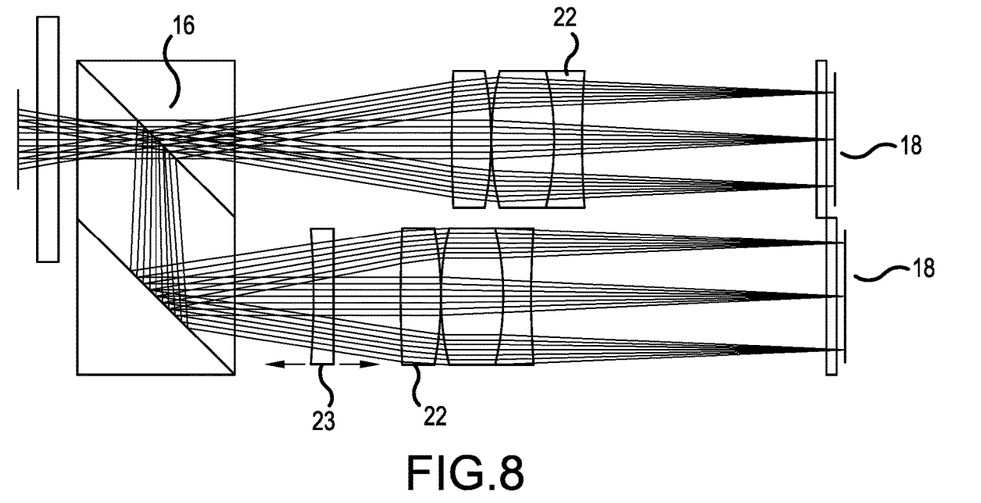
FIG. 8 shows an imaging head with a moveable lens for an endoscope.

The camera head can also be simplified by replacing the variable liquid lens 20 with a simple movable focusing lens 23 as shown in FIG. 8. This movable lens 23 can change the focus position or adjust the focal plane but cannot vary in focal power as can variable liquid lens 20. Otherwise, the system of FIG. 8 is substantially the same as that of FIG. 7 with similar capabilities.

Figure 9:
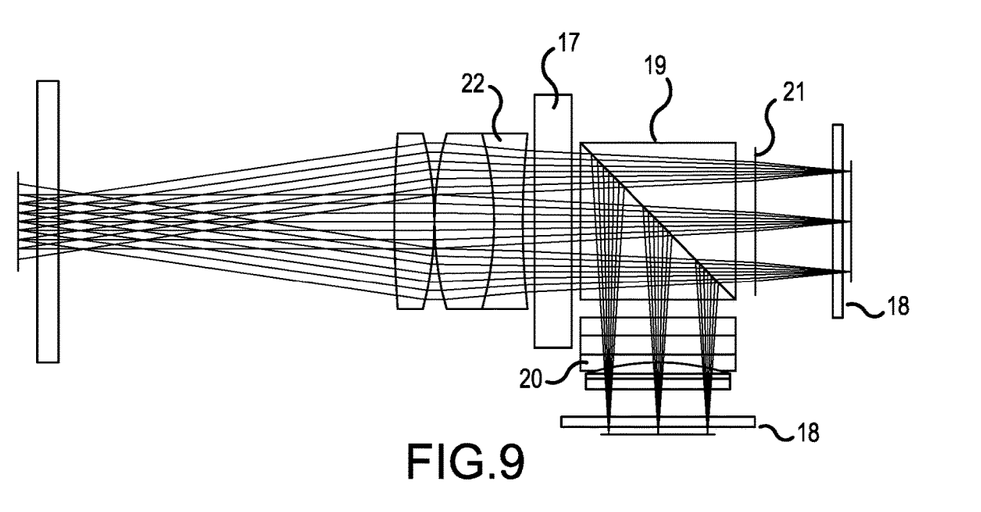
FIG. 9 shows an alternatively arranged imaging head of an endoscope.

Another optical arrangement for providing depth of field, as in the previous arrangements, is shown in FIG. 9. In this configuration, the variable liquid lens 20 are placed after a single beam splitter 19. Thus, the light beam received from the endoscope first passes through a collimating lens group 22 and a variable wave plate 17 then into the beam splitter 19 where the light beam is divided into two beams. The first beam passes straight through the beam splitter and a spectral filter 21 to the image sensor 18 and is captured. The second beam is deflected at a right angle and passes through the variable liquid lens 20 where the focal plane of the beam is changed. The second beam is then received and captured by a separate image sensor 18.

The arrangement in FIG. 9 is capable of imaging two or more images of different focal planes per acquisition period. Additional focal planes can be acquired subsequently by adjusting the variable liquid lens 20 between each image capture. Furthermore, the position of each image sensor 18 of FIG. 7-9 can be adjusted based on the endoscope being attached, environmental variables or object distance.

The camera head can identify the endoscope being attached and store in memory or adjust automatically based on a detection of a specific endoscope type, where the variable liquid lens 20 or the relative positions of the sensors 18 are adjusted. In either case, the adjustment preferably optimizes the focal offset introduced by these elements. Furthermore, the ray bundles at the focal planes should be telecentric.

Figure 10:
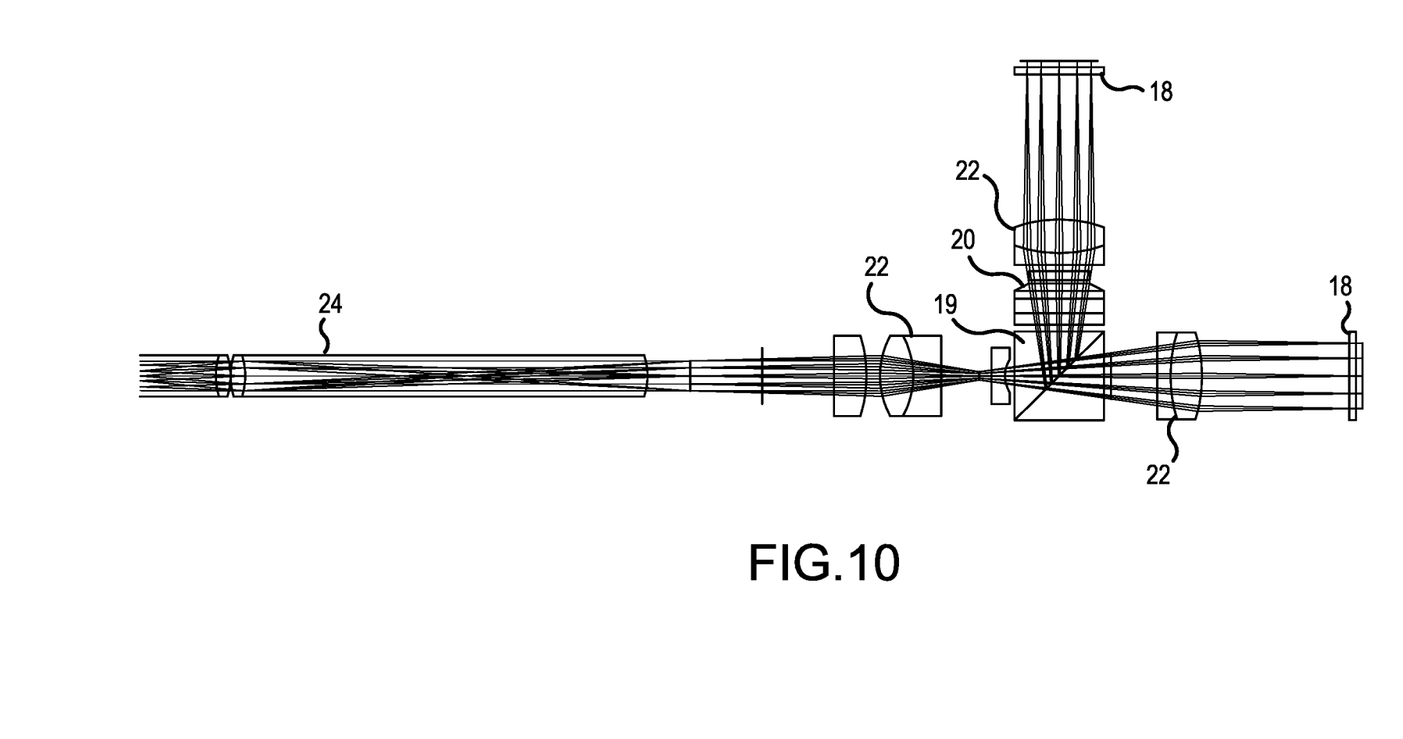
FIG. 10 shows an endoscope imaging head and a connection to an insertion end of the endoscope.

The larger system diagram of FIG. 10 illustrates how any of the camera heads disclosed herein would interact with an endoscope optical head 24. In the illustrated case, the variable liquid lens 20 is placed after the beam splitter 19. In addition, two collimating lens groups 22 are placed downstream of the beam splitter 19. The rod lens endoscope 24 could be any conventional endoscope or one specially adapted to identify with the disclosed camera head. In addition, a collimating lens group 22 is disposed upstream from the beam splitter 19 to control and adapt the light beam received from the endoscope.

Figure 11:
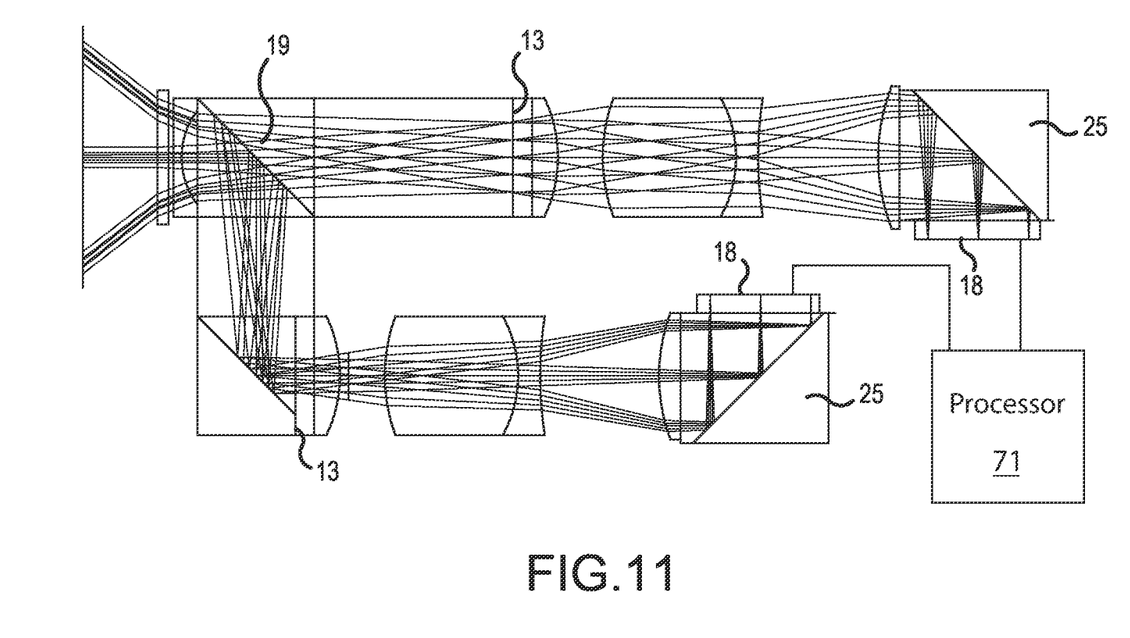
FIG. 11 shows an alternatively arranged imaging head of an endoscope.

An alternative arrangement without variable liquid lenses 20 is provided in FIG. 11 for a simpler structure and cheaper camera head of an endoscope. The incoming light beam is split into two beams by a beam splitter 19. Each beam then passes through an aperture stop 13, each aperture stop 13 having a different diameter. The difference in diameters produces images with distinct depth of field and resolution characteristics. Each beam then passes through carrier lenses before being collimated and reflected by the respective mirrors 25 onto the sensors 18. Lenses can also be disposed immediately upstream of the mirrors 25 to differently focus the light beams so that the sensors 18 can be mounted directly to the mirror blocks 25 at equal distances.

Additionally, variable apertures could be used to vary the attributes, namely the depth of field and resolution of the captured images at a given focal plane from one acquisition period to the next. From a manufacturing perspective, fixed apertures, and even variable apertures, can be less expensive and faster to position than variable liquid lenses.

Figure 12:
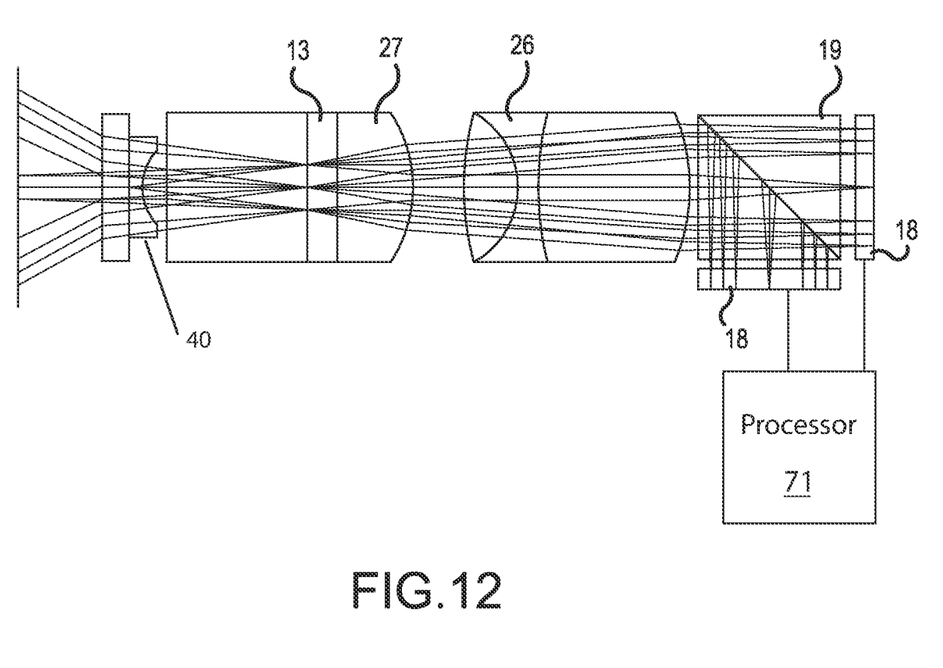
FIG. 12 shows a segment of an alternatively arranged endoscope.

The alternate optical configuration of FIG. 12 focuses incoming light via objective lens 40 (or collects relayed light from an attached endoscope) and passes the light beam through an aperture stop 13 and an aspheric or positive lens 27 and a collimating or carrier lens 26. The light beam is then split by beam splitter 19 and captured by sensors 18. Since each sensor 18 is offset from the beam splitter at different distances, two focal planes can be captured. The aperture stop 13 can also be a variable aperture stop and thus additional depth of field and resolution information when varied over multiple acquisition periods. Alternatively, the aperture stop 13 can be the variably-polarized aperture stop shown in FIG. 14 and further discussed below.

Digital image processing can combine each of the differently focused and separately captured images by selecting and extracting the sharp areas of each image and combining them into a single full resolution image. Additionally, the color information from the blurred areas can be reconstructed using the contrast information of the sharp areas or the combined image such that the colors are accurately reproduced.

First the fusion method generates a contrast weight map, a saturation weight map and an exposure weight map for each captured image. Then these maps are applied to select the best pixels from each image. Finally, the separate weighted images containing the selected or weighted pixels are combined with pyramid-based image fusion to generate a combined image.

By interpolating the color information, both resolution and contrast are slightly reduced. This, however, should not present a problem since the resolution of the sensors and combined image exceeds the resolution of the best endoscopes. On the other hand, the increased depth of focus allows for certain errors in the optics such as image field curvature to be compensated. Image field curvature often occurs in endoscopes with a very long inversion system.

Figure 13:
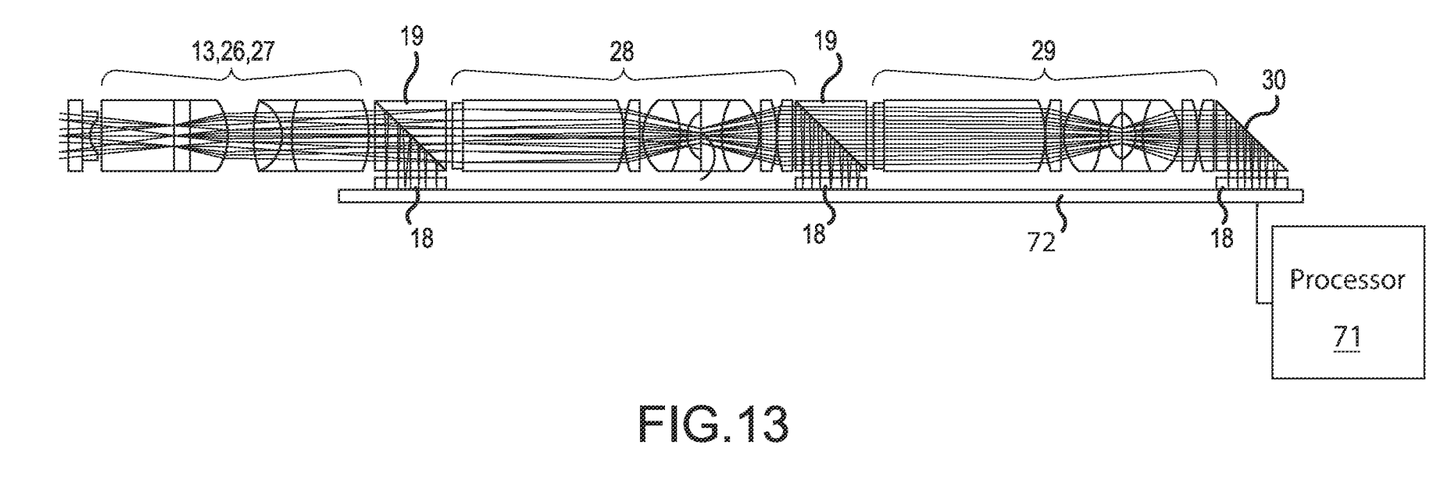
FIG. 13 shows several segments in a series arrangement.

The extended camera head of FIG. 13 with a first segment including elements 26 and 27, second segment 28 and third segment 29. The first segment includes an aperture 13, an aspheric lens 27 and a collimating lens 26 as may the camera head in FIG. 12. The beam splitter 19 at the end of the first segment splits one third of the light onto a sensor 18 and allows two-thirds of the light to pass through. Or, to compensate for surface losses or other differences, the reflective surfaces inside the beam splitters 19 may divide the beams unequally.

The second segment 28 is an inversion system carrying the remaining light beam to a second beam splitter 19 which splits half or some fraction of the remaining light onto another sensor 18 in a different focal plane. The remaining one-third of the light beam passes through the third segment 29 which is an inversion system like that in the second segment 28. The remaining light is deflected by mirror 30 and imaged by sensor 18, which is also in a different focal plane. Each inversion system flips the image or changes the parity of the image resulting in various captured image orientations which must be corrected optically or digitally.

The three sensors 18 in FIG. 13 are oriented such that all three can be soldered on the same board 72. In this way a very compact construction is possible which can be accommodated in a video endoscope without changing the housing or form factor of the device. Where appropriate, the deflecting mirror 30 can be replaced with another beam splitter 19 to pass on some of the beam to an additional inversion system for further imaging, and so on. In this case, the reflectance of each beam splitter 19 in the chain can be adjusted to equalize the light intensity imaged by each of the sensors 18.

The loss of light due to the distribution of the light beam onto various sensors may be compensated in that the system can have a higher numerical aperture than an equivalent system, that is a system which covers the same depth of focus with a single sensor as this system does with multiple sensors.

With the higher numerical aperture, overall a higher resolution is achieved while in conventional systems this high resolution requires a trade-off of lower depth of field. Due to the fact that in the various optical arrangements above the same image is captured by various sensors at the same time on different focal planes, the sharp areas of the individual sensors can be combined into one image.

Figure 14:
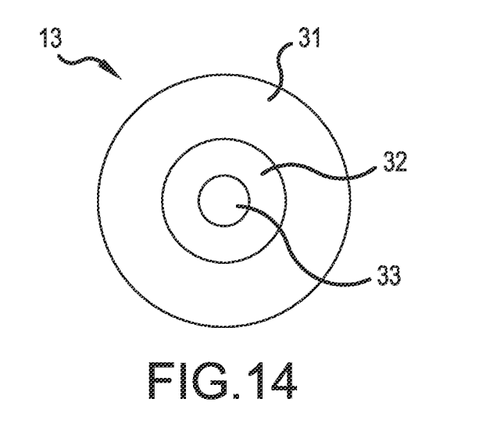
FIG. 14 shows an aperture.

The camera head for an endoscope shown in FIG. 12 can further include a specialized variably-polarized aperture stop 13 such as that shown in FIG. 14. This aperture stop 13 includes an outer opaque annular region 31, an inner polarizing annular filter 32, and an innermost circular opening 33 with no filter. This graduated aperture provides different f-numbers for beams of polarized and non-polarized light.

A beam exiting the aperture 13 of FIG. 14 is a separable beam including two overlapping beams propagating together until divided by a polarized beam splitter. After separation, one beam has a higher f-number than the other beam. Thus, one beam can be imaged at high resolution and the other beam can be image at a high depth of field. A processing unit can then calculate a single image with a higher depth of field and/or higher resolution than would be possible with a single sensor and conventional optical arrangements. The effect can be increased if the sensors 18 are in different focal planes. Alternatively, the polarizing filter 32 can be a spectral filter. In addition, more levels or annular regions within the graduated aperture of FIG. 14 are also advantageous.

Figure 15:
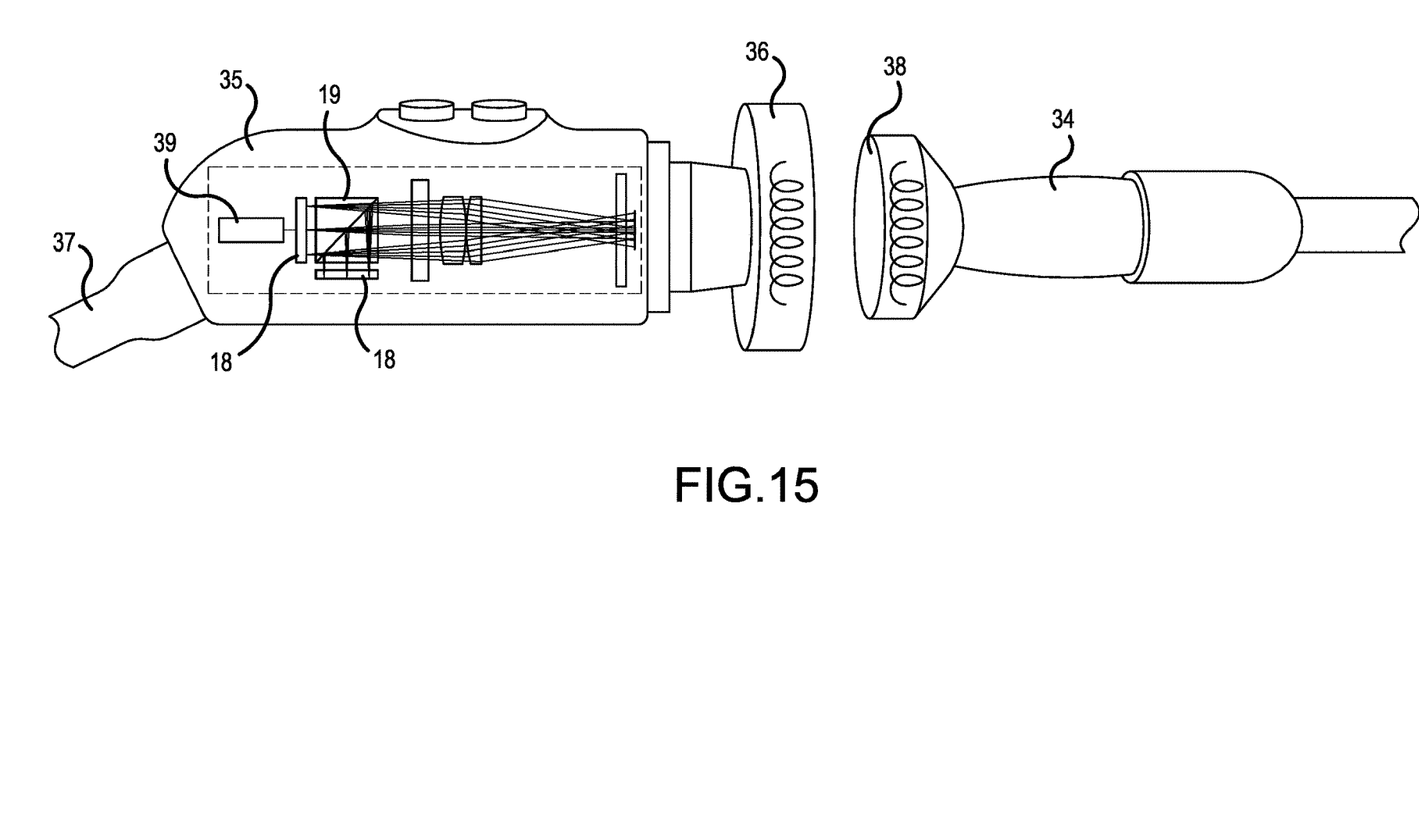
FIG. 15 shows an imaging head for connection to the insertion head.

The outlined device in FIG. 15 shows an exemplary camera head with a specialized Radio Frequency Identification (RFID) reader unit 36 for detecting an RFID identifier (or tag) 38 for a specific endoscope type 34. The camera head is surrounded by a handle structure 35 for easy handling by the operator. The digital signals from the sensors are then sent via connecting line 37 to a processing unit or display unit. Alternatively, the digital processing of the sensor images can be performed in the handle with only a combined image being sent to the display.

Advantageously, one or more of the image sensors 18 can be connected to a small actuator 39 that can adjust the focal plane position. This allows the focal plane difference between the two sensors to be adjusted for a particular situation without a variable liquid lens. The actuator 39 can also be combined with these other modes to provide larger ranges of focal plane differences.

Upon the identification of the specific endoscope 34 from the tag 38 on the proximal end of the endoscope, the actuator 39 adjusts the focal planes of the sensors 18 to an optimal focal plane offset. Alternatively, the identification can be done via the camera head with a QR code, bar code, or a specific color scheme on the endoscope end. Additionally, the endoscope could be identified by direct connection via a data bus or by analysis of electrical resistance or a magnetic field direction of the endoscope end.

The actuator 39 can be a piezo-electric motor or other small motor. Upon identification of the endoscope tag 38, a RFID reader 36 of a camera head like that in FIG. 12 signals a controller for the variable aperture stop 13. The variable aperture stop 13 is preferably disposed before the beam splitter 19 for adjustment to an optimal focal plane offset. Alternatively, the controller could be linked to a variable liquid lens 20 if the shown camera head was replaced with the camera head of FIG. 4.

It is also noted that any of the camera heads and optical arrangements disclosed herein may be implemented into the device of FIG. 15. The combined image from the several sensors of any of the camera heads will preferably be calculated in real time for an image with increased depth of field and increased resolution. If this is not possible, then a real time average value of the images super-imposed on each other can be generated with the calculated image being available later. In addition, three-dimensional modeling from the different focal planes can be calculated either in real time and displayed on a three-dimensional display or calculated and generated later for analysis and diagnosis.

The invention being thus described, it will be obvious that the same may be varied in many ways. For instance, capabilities, components or features from each of the optical arrangements above are combinable or transferrable to any of the other optical arrangements disclosed herein. Such variations are not to be regarded as a departure from the spirit and scope of the invention, and all such modifications as would be obvious to one skilled in the art are intended to be included within the scope of the following claims.

The invention claimed is:

1. An imaging apparatus for an endoscope, comprising:
a variable aperture stop receiving a light beam, wherein the variable aperture stop includes a first diameter defined by the variable aperture stop, and wherein an annular polarized filter is disposed in the variable aperture stop defining a second diameter;
a beamsplitter for separating the light beam received from the aperture stop based on polarization;
a first image sensor spaced apart from a first side of the beamsplitter at a first distance;
a second image sensor spaced apart from a second side of the beamsplitter at a second distance, wherein the first and second distances are not the same; and
an imaging processor receiving image data from the first and second image sensors, the imaging processor configured to combine the received image data from the first and second image sensors, such that in-focus regions of the received image data are combined to produce a resulting image with extended depth of field and/or improved resolution.

2. The imaging apparatus of claim 1, wherein the variable aperture stop is also temporally variable.

3. The imaging apparatus of claim 2, wherein the image processor is further configured to process images captured by the first and second image sensors, collected at a first acquisition period, and images captured by the first and second image sensors at a subsequent second acquisition period into the resulting image.

4. The imaging apparatus of claim 3, wherein the image processor is so configured to process the resulting image such that it has a depth of field greater than that of any of the individually collected images, has a region of resolution at least equal to that of any of the individually collected images, and a has resolution greater than either each of the images captured at the first acquisition period or each of the images collected at the second acquisition period.

5. The imaging apparatus of claim 2 further comprising a radio frequency identification (RFID) reader to detect an RFID identifier from the endoscope when the endoscope is attached to an imaging head and the image processor identifies properties associated with the attached endoscope based on the detected RFID identifier, wherein a diameter of the aperture is adjusted in response to the identified properties of the attached endoscope.

6. The imaging apparatus of claim 1, further comprising a radio frequency identification (RFID) reader to detect an RFID identifier from the endoscope when the endoscope is attached to an imaging head.

7. The imaging apparatus of claim 6 wherein the imaging processor identifies properties associated with the attached endoscope based on the detected RFID identifier.

8. The imaging apparatus of claim 1, wherein an imaging head is detachably connectable to an external endoscope.

9. The imaging apparatus of claim 1, wherein the image processor is so configured to process the resulting image such that it has a depth of field greater than that of any of the individually collected images and has a region of resolution at least equal to that of any of the individual images.

10. The imaging apparatus of claim 1, further comprising an objective lens, capturing light from an image scene and directing the captured light through the variable aperture stop.

11. The imaging apparatus of claim 10, further comprising an aspheric or positive lens receiving the light beam after passing from the variable aperture stop.

12. The imaging apparatus of claim 11, further comprising a collimating or carrier lens, receiving light from the aspheric or positive lens and passing the beam to the beam splitter.

13. An imaging apparatus for an endoscope, comprising:
an variable aperture stop receiving a light beam;
a beamsplitter for separating the light beam received from the aperture stop;
a first image sensor spaced apart from a first side of the beamsplitter at a first distance;
a second image sensor spaced apart from a second side of the beamsplitter at a second distance, wherein the first and second distances are not the same;
a radio frequency identification (RFID) reader to detect an RFID identifier from the endoscope when the endoscope is attached to an imaging head; and
an imaging processor receiving image data from the first and second image sensors, the imaging processor configured to combine the received image data from the first and second image sensors, such that in-focus regions of the captured images are combined to produce a resulting image with extended depth of field and/or improved resolution.

14. The imaging apparatus of claim, 13 wherein the imaging processor identifies properties associated with the attached endoscope based on the detected RFID identifier.

* * * * *